US008715203B2

(12) United States Patent
Palti

(10) Patent No.: US 8,715,203 B2
(45) Date of Patent: May 6, 2014

(54) COMPOSITE ELECTRODE

(75) Inventor: Yoram Palti, Haifa (IL)

(73) Assignee: Novocure Limited, St. Helier (JE)

( * ) Notice: Subject to any disclaimer, the term of this patent is extended or adjusted under 35 U.S.C. 154(b) by 1219 days.

(21) Appl. No.: 11/856,277

(22) Filed: Sep. 17, 2007

(65) Prior Publication Data

US 2009/0076366 A1   Mar. 19, 2009

(51) Int. Cl.
*A61B 5/103*   (2006.01)
*A61B 5/00*   (2006.01)
*A61N 1/04*   (2006.01)

(52) U.S. Cl.
CPC .............. *A61B 5/441* (2013.01); *A61N 1/0408* (2013.01); *A61N 1/0476* (2013.01); *A61N 1/0492* (2013.01)
USPC ........... 600/549; 600/556; 607/142; 607/152; 607/148

(58) Field of Classification Search
USPC .................................................. 600/395, 549
See application file for complete search history.

(56) References Cited

U.S. PATENT DOCUMENTS 4,809,707 A * 3/1989 Kraft et al. .................... 600/549
2003/0029569 A1 * 2/2003 Natsuhara et al. ....... 156/345.51

* cited by examiner

*Primary Examiner* — Carl H Layno
*Assistant Examiner* — Jon Eric C Morales
(74) *Attorney, Agent, or Firm* — Proskauer

(57) ABSTRACT

An electrode for applying electric fields to a patient includes a plurality of ceramic elements (e.g., ceramic discs) that are designed to be positioned against the patient's skin. Electrical connections are made to the ceramic elements (e.g., using a flex circuit). Temperature sensors (e.g., thermistors) are preferably provided at at least some of the ceramic elements to sense the temperature at the skin beneath the ceramic elements, so that appropriate action can be taken if an overtemperature condition is detected.

27 Claims, 5 Drawing Sheets

COMPOSITE ELECTRODE

BACKGROUND

U.S. Pat. Nos. 7,136,699 and 7,146,210, each of which is incorporated herein by reference, describe treating tumors or other rapidly dividing cells with AC electric fields at particular frequencies and field strengths. This application relates to an improved electrode that is particularly well-suited for applying those electric fields.

DETAILED DESCRIPTION OF THE PREFERRED EMBODIMENTS

Figure 1:
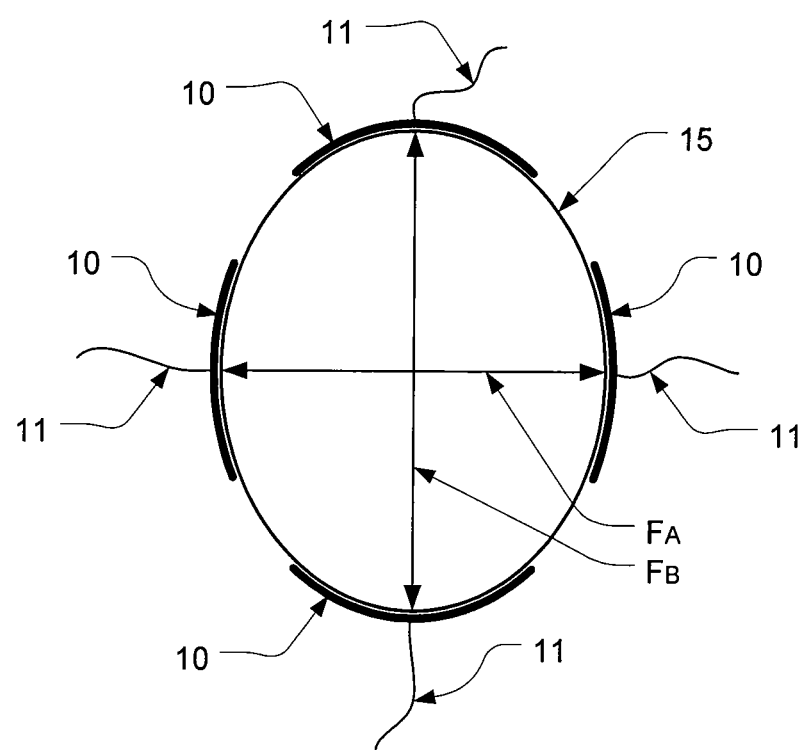
FIG. 1 shows a set of electrodes being used to apply electric fields to a subject.

FIG. 1 depicts a set of electrodes 10 that are used to apply electric fields to a body part 15 of a subject. Each of the electrodes 10 has at lead 11 associated therewith. As described in US Application No. 2005/0209642, which is incorporated herein by reference, a preferred approach for treating tumors using electric fields is to sequentially apply the field to the body part 15 being treated in different directions in an alternating pattern. One preferred approach to applying the field in different directions is to applying the field between a first set of electrodes for a period of time (e.g., ¼ second), then applying a field between a second set of electrodes for a period of time (e.g., ¼ second), then repeating that cycle for an extended duration (e.g., over a period of days or weeks). For example, with the electrode configuration depicted in FIG. 1, a horizontal electric field $F_A$ can be induced in the body part 15 by applying an AC voltage between the left and right leads 11 using an appropriate voltage source. Similarly, a vertical electric field $F_B$ can be induced in the body part 15 by applying an AC voltage between the top and bottom leads 11 using the same (or a different) voltage source.

Figure 2:
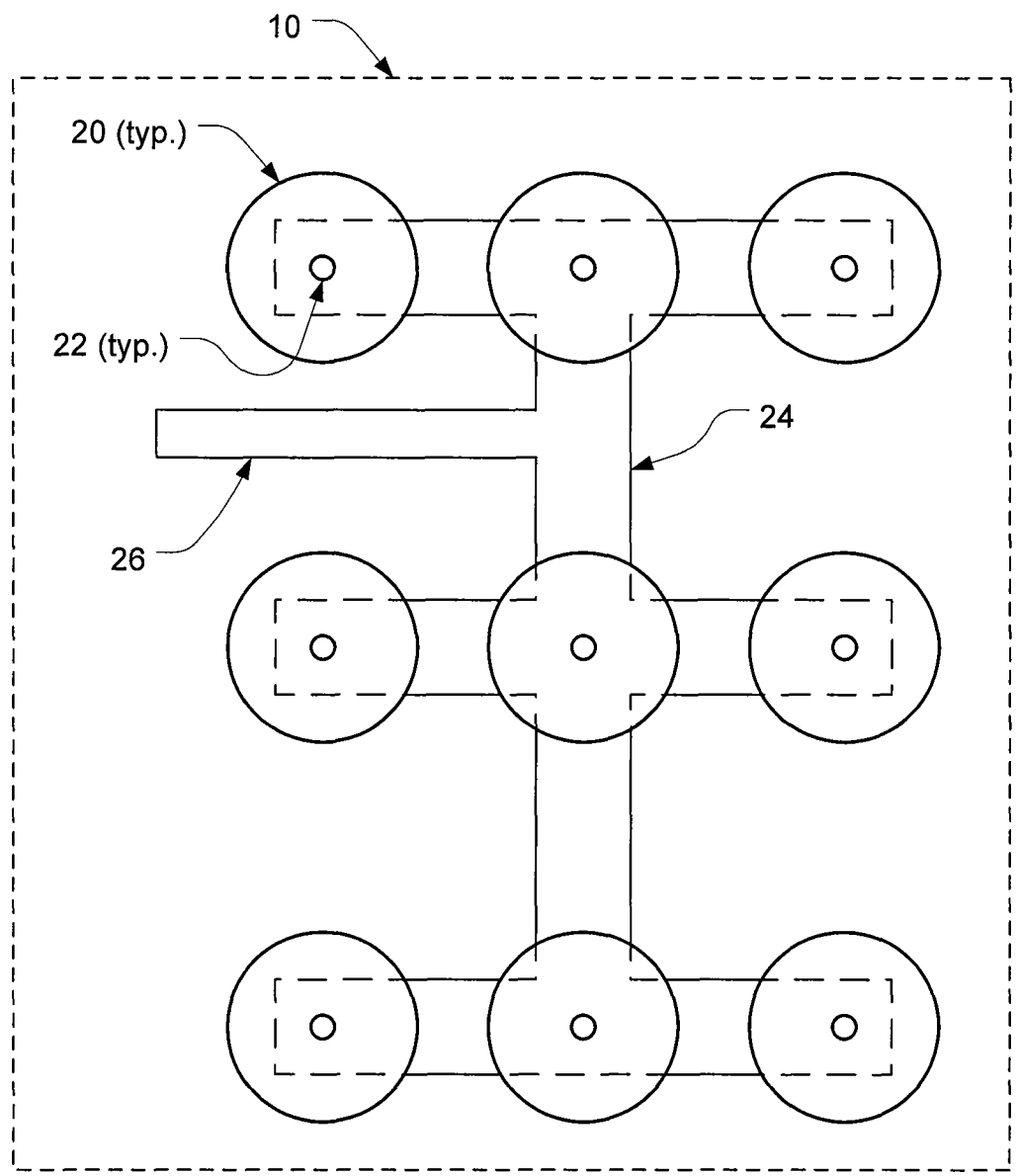
FIG. 2 is a mechanical schematic diagram of an electrode in accordance with a first embodiment of the invention.

FIG. 2 is a mechanical schematic diagram of a preferred embodiment of each of the electrodes 10. The electrode 10 includes a plurality of ceramic elements 20, each of which is preferably disc shaped. The ceramic elements 20 are preferably arranged in an array. Note that while FIG. 2 illustrates a 3×3 array of ceramic elements 20, arrays of other sizes maybe substituted therefor, such as a 2×2 array or a 2×3 array.

The ceramic elements 20 must be mechanical supported and electrical connections must be made to each element. A wide variety of approaches can be readily envisioned for mechanically supporting and electrically making connections to the ceramic elements 20. One preferred approach that performs both of these functions is to use a flex circuit 24 to both mechanically support the ceramic element 20 and provide the electrical connections. However, a wide variety of alternative approaches can be readily envisioned, including but not limited to discrete wiring, ribbon cable, etc.

Preferably, temperature sensors 22 are incorporated into the electrode 10, so that appropriate action (e.g., shutting off or lowering the AC voltage, or sounding an alarm) can be taken if an overtemperature condition is detected. In the illustrated embodiment a temperature sensor 22 is provided at each of the ceramic elements. However, in alternative embodiments temperature sensors may be provided only at selected ones of the ceramic elements 20. For example, when a 3×3 array of ceramic elements 20 are used, a temperature sensor may be provided for the eight outer ceramic elements 20, and omitted for the center ceramic element. When a flex circuit 24 is used to provide the electrically connection to the ceramic element, additional traces may provided on the flex circuit to interface with the temperature sensors 22.

Figure 3A:
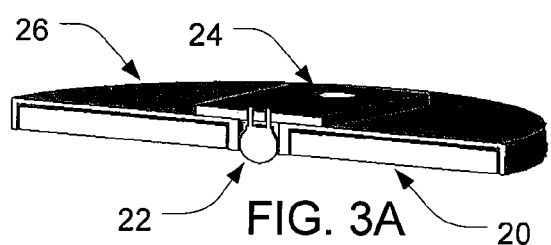
FIG. 3A is a cross section view of a subsection of the electrode shown in FIG. 2.

FIG. 3A is a cross section view of one of the ceramic elements 20 with a temperature sensor 22. Each of the ceramic elements 20 preferably has a conductive backing on the side that faces away from the patient, and this conductive backing is electrically connected to a contact on the flex circuit 24 using any conventional technique (e.g., solder). The conductive backing of the ceramic elements 20 may be implemented by using a ceramic disc that is silvered on one side. A cap 26 is preferably provided to mechanically support each of the ceramic elements 20. The caps are preferably made of an insulating material e.g., plastic.

In one preferred embodiment, the ceramic elements 20 are implemented using EC99 discs that are about 2 cm in diameter and are silvered on the side that faces away from the patient. In alternative embodiments, the ceramic discs 20 are implemented using ceramic discs that are between about 1.5 cm and about 2.5 cm, with a capacitance of art least 10 nF per disc, so as to provide an array with a capacitance of at least 120 nF. In alternative embodiments, higher capacitance discs may be used (e.g., at least 15 or at least 20 nF per disc). Preferably, the resistance of the ceramic discs should be as high as possible, and they should have a dielectric breakdown voltage of at least 4000 V.

Preferably, the ceramic elements 20 and the caps 26 have holes at their centers that are sized to accommodate the temperature sensors 22. The temperature sensors are preferably positioned in these holes, and the leads are mounted and electrically connected to respective traces on the flex circuit 24.

In some preferred embodiments, a thermistor is used as the temperature sensor, in which case two solder connections are needed to connect each thermistor to the flex circuit 24—one for each lead. However, persons skilled in the relevant arts will appreciate that a wide variety of alternative temperature sensors other than thermistors may also be used, including but not limited to temperature sensing integrated circuits, RTDs, etc. In some preferred embodiments, type NTC thermistors in a surface-mount package are used, with a nominal resistance value of 10 kΩ at 25° C. The operating range is preferably wide enough to sense the expected range temperatures (e.g., from 20-50° C.). Of course, wider operating ranges (e.g., −40° C. to 150° C.) may also be used.

Figure 3B:
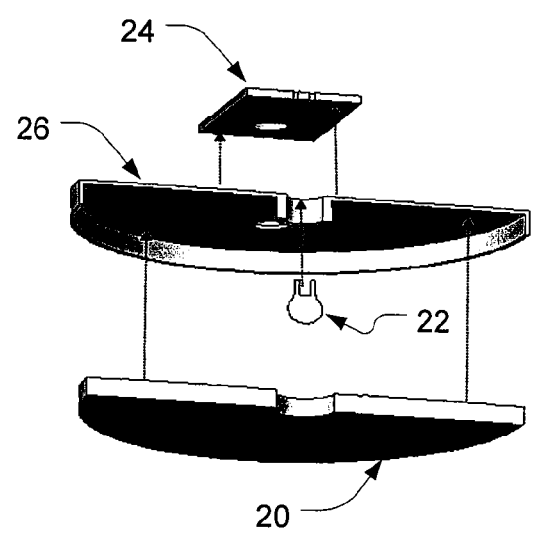
FIG. 3B is an exploded cross section view of the same subsection of the electrode.
Figure 3C:
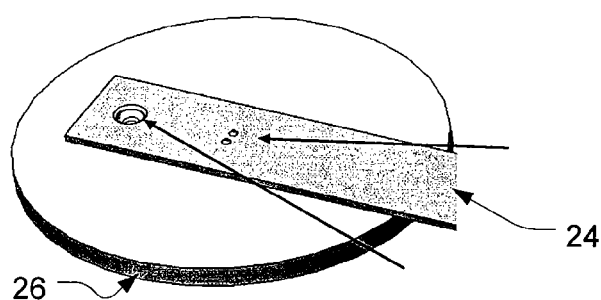
FIG. 3C is a rear view of the same subsection of the electrode.

FIG. 3B is an exploded view of the same components depicted in FIG. 3B, and FIG. 3C is a rear view of the same components. Note, however, that in the FIG. 3C view, the ceramic disc 20 and the temperature sensor 22 are obscured by the cap 26.

Figure 4:
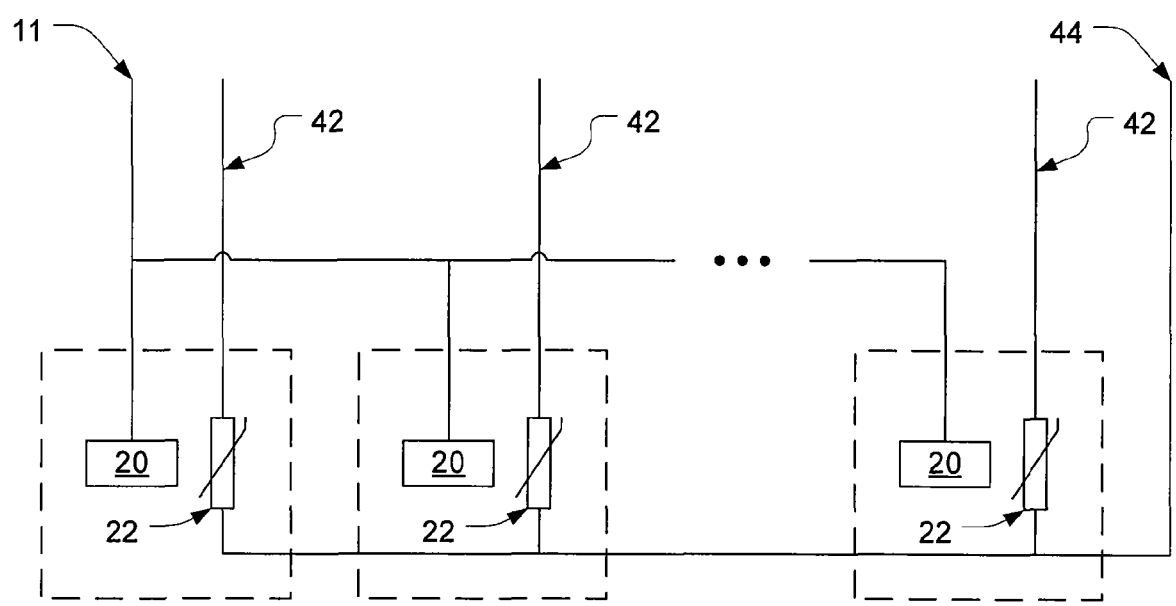
FIG. 4 is an electrical schematic of the electrode shown in FIG. 2.

FIG. 4 is an electrical schematic depicting how the various components of the electrode are connected, in an embodiment where the temperature sensors are implemented using thermistors. The main lead 11 is connected to one side of each of the ceramic elements 20, and the other side of each of the ceramic elements 20 is exposed for placement against the patient's body. When a pair such electrodes are applied to a patient's body, an AC voltage is applied between the main lead 11 of a first electrode and a main lead (not shown) of a similar electrode (not shown). An electric field is generated between the ceramic elements of the first electrodes (depicted in FIG. 4) and the second electrode (of similar configuration). As discussed above, temperature sensors 22 are preferably provided at some or all of the ceramic elements. Preferably, the temperature sensors are configured so that an individual temperature reading can be obtained from each temperature sensor 22. One way to implement this in embodiments that use thermistors for the temperature sensors is to route a lead 42 from one end of each of the thermistors to external circuitry (not shown), and use a common return lead 44 that is shared by all the thermistors. Any conventional circuitry for interfacing with the thermistors may be used.

Of course, persons skilled in the relevant arts will recognize that when alternative temperature sensors are used, the electrical interface to the temperature sensor will have to be adjusted accordingly from the one depicted in FIG. 4. For example, if temperature sensing integrated circuits that communicate over a serial interface bus are used, an appropriate power supply and serial bus must be provided, the implementation of which will be apparent to persons skilled in the relevant arts.

Figure 5:
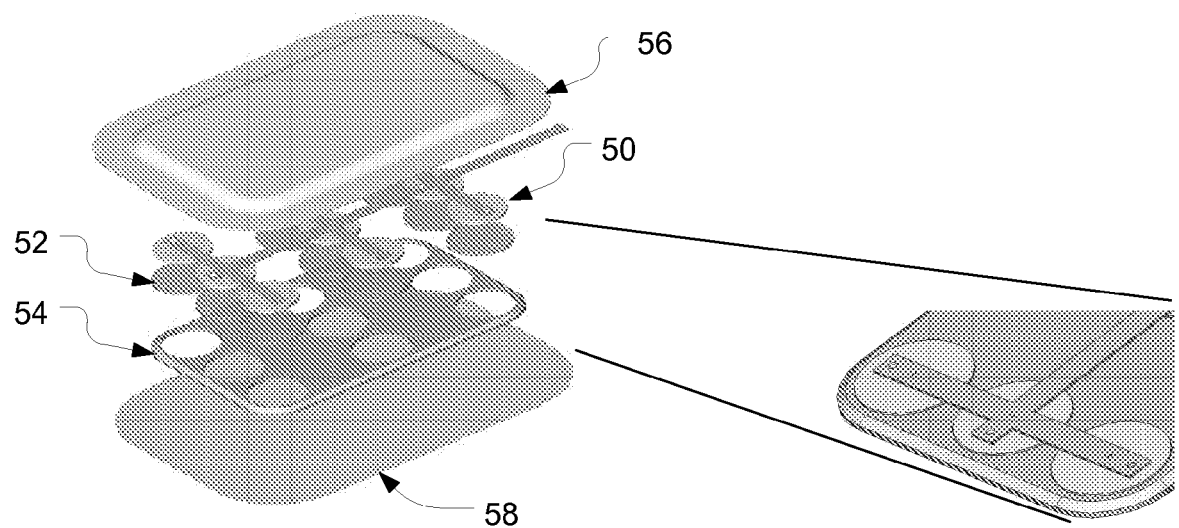
FIG. 5 is a perspective view of the electrode shown FIG. 2 together with a preferred set of accessories for use therewith.

FIG. 5 depicts an electrode that is similar to the electrode 10 discussed above in connection with FIGS. 2-4, together with a preferred set of accessories for use therewith. The electrode 50 is preferably packaged with a layer 52 of biocompatible hydrogel (e.g., Amgel AG603) disposed beneath each of the ceramic discs, and the ceramic discs preferably rest in a filler layer 54 (e.g., 3M 1773 foam tape) with an adhesive bottom and cutouts dimensioned to accept the ceramic discs. A layer of adhesive tape 56 (e.g., 3M 1776 non-woven medical tape) is positioned above the electrode 50, with the adhesive side facing down towards the patient. The adhesive tape 56 preferably extends laterally beyond the electrode 50 and the filler layer 54. A peel-away backing 58 (e.g., #53 white poly-coated kraft paper) is provided beneath all the other components 52-56. To use the electrode, the backing 58 is peeled away, which exposes the bottom of the hydrogel layer 52, the adhesive bottom of the filler layer 54, and uncovered portions of the adhesive tape 56. That entire assembly is then pressed against the patient's skin (which has preferably been shaved) so as to adhere thereto. An electrical connection is then made to the electrode 50 using an appropriate electrical connector.

While the present invention has been disclosed with reference to certain embodiments, numerous modifications, alterations, and changes to the described embodiments are possible without departing from the scope of the present invention, as defined in the appended claims. Accordingly, it is intended that the present invention not be limited to the described embodiments, but that it has the full scope defined by the language of the following claims, and equivalents thereof.

I claim:

1. A composite electrode comprising:
   a plurality of ceramic elements, each of the ceramic elements having (a) a lower surface configured to rest on a patient's body and (b) an upper surface;
   a first lead;
   at least one electrical conductor configured to make a direct electrical connection between the upper surface of each of the ceramic elements and the first lead; and
   a support structure configured to mechanically connect the plurality of ceramic elements during use, with the lower surface of each of the plurality of ceramic elements resting on the patient's body.

2. The composite electrode of claim 1, further comprising at least one temperature sensor configured to sense the temperature beneath at least one of the ceramic elements.

3. The composite electrode of claim 1, wherein the least one electrical conductor and the support structure are both implemented using a flex circuit.

4. The composite electrode of claim 1, wherein the plurality of ceramic elements comprises at least 4 ceramic elements.

5. The composite electrode of claim 1,
   wherein the plurality of ceramic elements comprises at least 4 ceramic discs, each having a diameter between about 1.5 cm and about 2.5 cm and a capacitance of at least 2.0 nF, and
   wherein the least one electrical conductor and the support structure are both implemented using a flex circuit.

6. The composite electrode of claim 5, further comprising at least two thermistors configured to sense the temperature beneath at least two of the ceramic discs, respectively.

7. The composite electrode of claim 5, further comprising a covering disposed above the ceramic elements and the support structure, the covering having an adhesive lower surface that is configured to hold the ceramic elements and the support structure against the patient's body.

8. The composite electrode of claim 7, wherein the ceramic elements rest in a filler layer with an adhesive bottom and cutouts dimensioned to accept the ceramic elements.

9. The composite electrode of claim 8, further comprising at least one temperature sensor configured to sense the temperature beneath at least one of the ceramic elements.

10. The composite electrode of claim 9, wherein the ceramic elements are disc-shaped.

11. The composite electrode of claim 1,
    wherein the plurality of ceramic elements consists of nine ceramic discs, each having a diameter between about 1.5 cm and about 2.5 cm and a capacitance of at least 20 nF,
    wherein the least one electrical conductor and the support structure are both implemented using a flex circuit,
    and wherein the composite electrode further comprises at least four thermistors configured to sense the temperature beneath at least four of the ceramic discs, respectively.

12. The composite electrode of claim 1, wherein the direct electrical connection between the upper surface of each of the ceramic elements and the first lead is made using a flex circuit that is soldered to a conductive backing that is disposed on the upper surface of each of the ceramic elements.

13. A composite electrode comprising:
    at least four ceramic elements, each of the ceramic elements having (a) a lower surface configured to rest on a patient's body and (b) an upper surface;
    a first lead;
    at least one electrical conductor configured to make a direct electrical connection between the upper surface of each of the ceramic elements and the first lead; and
    a support structure configured to mechanically connect the ceramic elements during use, with the lower surface of each of the ceramic elements resting on the patient's body;
    at least two temperature sensors configured to sense the temperature beneath at least two of the ceramic elements, respectively;

a layer of electrically conductive hydrogel disposed on the lower surface of each of the ceramic elements;

a covering disposed above the ceramic elements and the support structure, the covering having an adhesive lower surface that is configured to hold the ceramic elements and the support structure against the patient's body.

14. The composite electrode of claim 13, further comprising a backing disposed beneath the ceramic elements, the support structure, and the covering, wherein the adhesive lower surface of the covering is easily removable from the backing.

15. The composite electrode of claim 13, wherein the temperature sensors comprise thermistors.

16. The composite electrode of claim 13, wherein the least one electrical conductor and the support structure are both implemented using a flex circuit.

17. The composite electrode of claim 13, wherein there are 9 ceramic elements.

18. The composite electrode of claim 13,
wherein there are 9 ceramic elements that are each round and have a diameter between about 1.5 cm and about 2.5 cm and a capacitance of at least 20 nF, and
wherein the least one electrical conductor and the support structure are both implemented using a flex circuit, and
wherein there are at least four temperature sensors configured to sense the temperature beneath at least four of the ceramic elements, respectively.

19. The composite electrode of claim 18, wherein the ceramic elements are disc-shaped.

20. The composite electrode of claim 19, wherein the ceramic elements have holes in their centers and the temperature sensors are positioned in the holes.

21. The composite electrode of claim 18, wherein the ceramic elements rest in a foam filler layer with an adhesive bottom and cutouts dimensioned to accept the ceramic elements.

22. The composite electrode of claim 13, wherein the ceramic elements are disc-shaped.

23. The composite electrode of claim 22, wherein the ceramic elements have holes in their centers and the temperature sensors are positioned in the holes.

24. The composite electrode of claim 13, wherein the ceramic elements rest in a filler layer.

25. The composite electrode of claim 13, wherein the ceramic elements rest in a filler layer with an adhesive bottom and cutouts dimensioned to accept the ceramic elements.

26. The composite electrode of claim 13, wherein the ceramic elements rest in a foam filler layer with an adhesive bottom and cutouts dimensioned to accept the ceramic elements.

27. The composite electrode of claim 13, wherein the direct electrical connection between the upper surface of each of the ceramic elements and the first lead is made using a flex circuit that is soldered to a conductive backing that is disposed on the upper surface of each of the ceramic elements.

* * * * *